(12) United States Patent
Dolbier, Jr. et al.

(10) Patent No.: US 6,919,484 B2
(45) Date of Patent: Jul. 19, 2005

(54) METHOD FOR INCORPORATION OF PENTAFLUOROSULFANYL ($SF_5$) SUBSTITUENTS INTO ALIPHATIC AND AROMATIC COMPOUNDS

(75) Inventors: William R. Dolbier, Jr., Gainesville, FL (US); Samia Aït-Mohand, Longueuil (CA); Tatiana Sergeeva, Duluth, MN (US)

(73) Assignee: University of Florida, Gainesville, FL (US)

( * ) Notice: Subject to any disclaimer, the term of this patent is extended or adjusted under 35 U.S.C. 154(b) by 79 days.

(21) Appl. No.: 10/627,831

(22) Filed: Jul. 24, 2003

(65) Prior Publication Data

US 2004/0106827 A1 Jun. 3, 2004

Related U.S. Application Data

(60) Provisional application No. 60/448,831, filed on Feb. 21, 2003, and provisional application No. 60/399,044, filed on Jul. 25, 2002.

(51) Int. Cl.$^7$ ............................................. C07C 381/00
(52) U.S. Cl. .......................................... 568/74; 568/38
(58) Field of Search ..................................... 568/38, 74

(56) References Cited

U.S. PATENT DOCUMENTS

| | | | |
|---|---|---|---|
| 3,102,903 A | | 9/1963 | Coffman et al. |
| 5,441,720 A | * | 8/1995 | Koppes et al. ............... 423/386 |
| 5,741,935 A | * | 4/1998 | Bowden et al. ................ 568/74 |

FOREIGN PATENT DOCUMENTS

| | | | |
|---|---|---|---|
| GB | 891 552 | | 3/1962 |
| GB | 905 006 | | 9/1962 |
| GB | 907 648 | | 10/1962 |
| WO | WO 99/22857 | * | 5/1999 |

OTHER PUBLICATIONS

Journal of Fluorine Chemistry by Winter vol. 107 p. 23–30 2001.*
Aït–Mohand, S. and W.R. Dolbier "New and convenient method for incorporation of pentafluorosulfanyl ($SF_5$) substituents into aliphatic organic compounds" *Organic Letters*, 2002, 4(17):3013–3015.
Bowden, R.D. et al. "A new method for the synthesis of aromatic sulfurpentafluorides and studies of the stability of the sulfurpentafluoride group in common synthetic transformations" *Tetrahedron*, 2000, 56:3399–3408.
Case, J.R. et al. "Sulpher Chloride Pentafluoride: Reaction with Unsaturated Hydrocarbons" *J. Chem. Soc.*, 1961, 2066–2070.
Chambers, R.D. and R. Spink, "Microreactors for elemental fluorine" *Chem. Commun.*, 1999, 883–884.
Fokin, A.V. et al. "Organic compounds containing a pentafluorothio group" *Russ. Chem. Bull.*, 1996, 45:2804–2806.
Hodges, A.M. et al. "ω–Pentafluoro–$\lambda^6$–sulfanyl($SF_5$)–$n$–perfluroalkyl benzene derivatives" *J. Fluorine Chem.*, 2001, 110:1–4.
Sheppard, W.A. "Arylsulfur Pentafluorides" *J. Am. Chem. Soc.*, 1962, 84:3064–3072.
Sidebottom, H.W. et al. "Free Radical Addition to Olefins" *Trans. Faraday Soc.*, 1969, 65:2103–2109.
Sipyagm, A.M. et al. "Preparation of the first *ortho*–substituted pentafluorosulfanylbenzenes" *J. Fluorine Chem.*, 2001, 112:287–295.
Wessel, J. et al., *Chem. Ber.*, 1983, 116:2399–2407.
Winter, R. and G.L. Gard "New pentafluorothio ($SF_5$) esters" *J. Fluorine Chem.*, 1994, 66:109–116.

* cited by examiner

*Primary Examiner*—Deborah D. Carr
(74) *Attorney, Agent, or Firm*—Saliwanchik, Lloyd & Saliwanchik

(57) ABSTRACT

The subject invention provides convenient, regiospecific and highly stereoselective addition of $SF_5Cl$ in high yield to a variety of alkenes and alkynes.

12 Claims, No Drawings

METHOD FOR INCORPORATION OF PENTAFLUOROSULFANYL (SF$_5$) SUBSTITUENTS INTO ALIPHATIC AND AROMATIC COMPOUNDS

CROSS-REFERENCE TO RELATED APPLICATIONS

This application claims the benefit of U.S. Provisional Application Ser. No. 60/448,831, filed Feb. 21, 2003, and also claims the benefit of U.S. Provisional Application Ser. No. 60/399,044, filed Jul. 25, 2002.

The subject invention was made with government support under a research project supported by the Air Force Office of Scientific Research, STTR Phase I Contract #F49620-01-C-0046. The United States government may have certain rights in this invention.

BACKGROUND OF INVENTION

There is currently great interest in methods for the preparation of selectively fluorinated organic compounds. This interest results from the profound influence that fluorine incorporation can have on the physical properties, chemical properties, and biological activity of molecules. For example, methods for putting the bulky, highly electronegative and generally inert trifluoromethyl group into organic compounds have received much research attention during recent years.

Another fluorinated substituent that could attract interest among synthetic organic chemists is the pentafluorosulfanyl (SF$_5$) group (Winter et al., *Inorganic Fluorine Chemistry—Toward the 21st Century* (1994) 555:128–47, Pub: American Chemical Society: Washington (Thrasher, J. S., Strauss, S. H., Eds.); Lentz et al., *Chemistry of Hypervalent Compounds* (1999) 295–326; Pub: Wiley-VCH: New York (Akiba, K., Ed.); Verma et al., *Advances in Inorganic Chemistry* (1994) 41:125–69, Pub: Academic Press: San Diego (Sykes, A. G., Ed.); pentafluorosulfanyl groups bear some similarity to trifluoromethyl groups, however, SF$_5$ is more electronegative ($\sigma_p$=+0.68 versus +0.54 for CF$_3$; Sheppard, W. A., *J. Am. Chem. Soc.* (1962) 84:3072–6) and more sterically demanding.

However, until the development of the subject invention, methods for the addition of an SF$_5$ substituent to a benzene ring or other aliphatic compounds were inconvenient, dangerous, and many methods required the use of elemental F$_2$ or oxidative fluorination by AgF$_2$ (Sheppard, W. A., *J. Am. Chem. Soc.* (1962) 84:3064–3072; Chambers et al., *Chem. Commun.* (1999) 883–884; Bowden et al., *Tetrahedron* (2000) 56:3399–3408; Sipyagin et al., *J. Fluorine Chem.* (2001) 112:287–295) to incorporate an SF$_5$ group into aliphatic compounds (i.e., the methodologies relied on high pressure autoclave or specialized photochemical procedures) (Case et al., *J. Chem. Soc.* (1961) 2066–2070; Wessel et al., *Chem. Ber.* (1983) 116:2399–2407; Winter et al., *J. Fluorine Chem.* (1994) 66:109–116; Fokin et al., *Russ. Chem. Bull.* (1996) 45:2804–6). Thus, the introduction SF$_5$ into aliphatic compounds has not been widely practiced by synthetic organic chemists.

SF$_5$Cl is presently the only commercially available "reagent" that can be used to introduce the SF$_5$ substituent into aliphatic compounds. As a gaseous pseudo halogen, this reagent cannot be used as an electrophilic source of SF$_5$. It has, however, been used in free radical chain alkene/alkyne addition processes (Sidebottom et al., *Trans. Faraday Soc.* (1969) 65:2103–2109). These processes are generally done thermally, in an autoclave, with or without an initiator, or using room temperature gas phase or low temperature solution phase photochemical processes. For example (Case et al., *J. Chem. Soc.* (1961) 2066–2070):

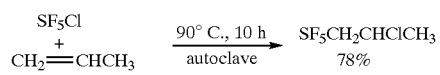

In order for SF$_5$-derivatives to become incorporated into the day-to-day strategic planning of working synthetic organic chemists, a convenient bench-top procedure for the introduction of SF$_5$ substituents into organic substrates is needed. The subject invention provides such a method—one that will allow convenient addition of SF$_5$Cl to a large variety of aliphatic compounds (such as alkenes and alkynes) in excellent yield.

BRIEF SUMMARY

The subject invention provides methods for the convenient addition of pentafluorosulfanyl substituents into aliphatic organic compounds. In various embodiments, pentafluorosulfanyl substituents are incorporated into pharmaceutical compounds or agrochemical compounds containing aliphatic groups. An exemplary reaction is:

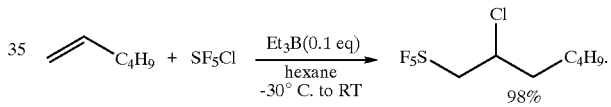

DETAILED DISCLOSURE

The subject invention provides methods for the convenient addition of pentafluorosulfanyl substituents into aliphatic organic compounds. In various embodiments, pentafluorosulfanyl substituents are incorporated into pharmaceutical compounds or agrochemical compounds containing aliphatic groups. The invention also provides aromatic SF$_5$ substituted compounds and methods of preparing such compounds comprising the addition of SF$_5$Cl to cyclohexene and cyclohexadiene derivatives followed by elimination/oxidation steps.

The simplicity of new method provided by the subject invention, combined with the generally excellent yields that are obtained, constitutes a breakthrough in SF$_5$ synthetic methodology that opens the door to the convenient, bench top preparation of a multitude of SF$_5$-containing aliphatics by synthetic organic chemists. Thus, the subject invention has application to broad applicability to any compound containing aliphatic groups, including functionalized or substituted compounds.

Exemplary compounds into which pentafluorosulfanyl substituents can be incorporated include those compounds containing one or more functional groups selected from the group consisting of substituted or unsubstituted aliphatic groups, substituted or unsubstituted aromatic groups, substituted or unsubstituted alicyclic groups, substituted or unsubstituted alkene groups, substituted or unsubstituted alkyne groups, substituted or unsubstituted styrene groups, disubstituted alkene groups (e.g., 2,2-disubstituted alkenes), substituted or unsubstituted non-terminal alkene groups, substituted or unsubstituted non-terminal alkyne groups, cyclohexene groups, substituted cyclohexene groups, cyclohexadiene groups, substituted cyclohexadiene groups, and combinations of such functional groups, or derivatives of the aforementioned functional groups. These compounds may also be referred to as compounds of interest within this specification.

In various embodiments, pharmaceutical compounds or agrochemical compounds (e.g., herbicides, insecticides, pesticides, vermin poisons) comprising one or more aliphatic, aromatic, alicyclic, alkene, alkyne, styrene, disubstituted alkene, non-terminal alkene, or non-terminal alkyne functional groups can be treated according to the subject process to incorporate pentafluorosulfanyl substituents into their respective structures. The mildness of the alkylborane, dialkylborane, trialkylborane, and/or 9-borabicyclo[3.3.1] nonane-catalyzed reaction conditions contributes to the broad applicability of the methods provided by the subject invention.

With a boiling point of −21° C., $SF_5Cl$ is readily condensed into hexane which, in some embodiments, contains the aliphatic, aromatic, alicyclic, alkene, or alkyne substrate of interest. When an initiator or catalyst is added (e.g., by syringe), an immediate reaction is evident, and, for many substrates, the reaction is effectively complete after 30 minutes. Initiators/catalysts suitable for use in the subject invention include alkylboranes, dialkylboranes, trialkylboranes, and/or 9-borabicyclo[3.3.1]nonane; alternatively, one or more initiators/catalysts (e.g., various combinations of the aforementioned initiators/catalysts) can be used in the methods taught herein. The terms initiator and catalyst may be used interchangeably in the context of the subject invention. Solutions containing $SF_5Cl$ and/or compounds of interest can be maintained at temperatures of about −20° C. to −40° C., −30° C. to −40° C., or −20° C. to −30°C.

Thus, the subject invention provides novel pentafluorosulfanyl substituted compounds and methods of making pentafluorosulfanyl substituted compounds. The subject invention also provides for the production of $SF_5Cl$ compounds that have been enantiomerically enriched according to methods known in the art. Substituted compounds according to the subject invention can be made by adding of $SF_5Cl$ to hexane to form a $SF_5Cl$ containing hexane solution, contacting a hexane solution comprising one or more compounds of interest containing one or more functional groups selected from the group consisting of substituted or unsubstituted aliphatic groups, substituted or unsubstituted aromatic groups, substituted or unsubstituted alicyclic groups, substituted or unsubstituted alkene groups, substituted or unsubstituted alkyne groups, substituted or unsubstituted styrene groups, disubstituted alkene groups (e.g., 2,2-disubstituted alkenes), substituted or unsubstituted non-terminal alkene groups, substituted or unsubstituted non-terminal alkyne groups, cyclohexene groups, substituted cyclohexene groups, cyclohexadiene groups, substituted cyclohexadiene groups, and combinations of such functional groups, or derivatives of the aforementioned functional groups, with the $SF_5Cl$ hexane solution, and adding one or more catalyst(s)/initiator(s) selected from the group consisting of dialkylboranes, trialkylboranes, and 9-borabicyclo [3.3.1] nonane. The reactants are mixed and maintained under conditions suitable for the addition of pentafluorosulfanyl substituents to the compounds of interest. The reaction can be terminated at any point, however, allowing the reaction to proceed to completion results in increased yields of $SF_5$-substituted compounds. In embodiments where cyclohexenes (or derivatives thereof) and/or cyclohexadienes (or derivatives thereof) are substituted with $SF_5Cl$, elimination/oxidation steps may be used to form $SF_5$ aromatics.

Pentfluorosulfanyl substituted compounds may, optionally, be hydrolyzed and, optionally, dried over a suitable desiccant. The pentfluorosulfanyl substituted compounds can then, optionally, be passed over a short column (containing, for example, a sizing gel or silica gel) to remove contaminants (such as, for example, catalyst/initiator or unsubstituted compounds). Purity and/or analysis of the pentafluorosulfanyl substituted compounds of the invention can be determine using methods well-known to those skilled in the art, including, and not limited to, NMR analysis. In various embodiments, the catalyst(s)/initiator(s) may be added to one or more of a hexane solution containing $SF_5Cl$ or a hexane solution containing one or more compounds of interest prior to the combination of these hexane solutions.

A specific embodiment of the subject invention is directed to methods of synthesis for compounds substituted with pentafluorosulfanyl. A method of the subject invention is directed to contacting a hexane solution of one or more compounds with $SF_5Cl$ solution. Preferably, the compounds are unsaturated. More preferably, the unsaturated compounds are substituted or unsubstituted aliphatic or alicyclic alkenes or alkynes, where the substituents may be one or more aryl or alkyl groups that themselves may bear functional groups such as alkenes, alcohols, halogens, ketones, aldehydes, carboxylic acids, carboxyhic acid derivatives or other common organic functional groups.

The method further comprises contacting the resulting solution with one or more initiators. The initiator is selected from the group consisting of dialkylboranes, trialkylboranes, 9-borabicyclo[3.3.1]nonane, and mixtures thereof. The initiated injection of said compounds and said $SF_5Cl$ solution can proceed under conditions suitable for addition of pentafluorosulfanyl substituents to the compounds. Preferably, the reaction is allowed to proceed to completion.

Opiionally, the pentafluorosulfanyl substituted compounds can undergo climination or oxidation, hydrolysis, drying, and/or purification. Preferably, any drying is performed over a desiccant.

In another embodiment, the initiator is added to a hexane solution containing $SF_5Cl$ before the resulting solution is contacted with the one or more compounds. In yet another embodiment, the initiator is added to a hexane solution containing one or more compounds prior to the combination of the solution containing $SF_5Cl$ and the solution containing a compound.

A preferred method is directed to the synthesis of a pentafluorosulfanyl aromatic, specifically a pentafluorosulfanyl benzene. A combination of 4,5-dichloro-1-cyclohexene, $CH_2Cl_2$, $SF_5Cl$, and a catalyst selected from the group consisting of dialkylboranes, trialkylboranes, 9-borabicyclo[3.3.1]nonane, and mixtures thereof is prepared. The solvent is evaporated from the combination. The product produced thereby is contacted with a solution of sodium ethoxide(NaOEt in ethanol). Water is added to this solution, which is extracted. The extract is washed and dried over a desiccant. Solvent is evaporated from the extract, and pentafluorosulfanyl benzene is recovered.

Following are examples which illustrate procedures for practicing the invention. These examples should not be construed as limiting. All percentages are by weight and all solvent mixture proportions are by volume unless otherwise noted.

EXAMPLE 1

$SF_5$ Substituted Alkene Compounds

Into a three-necked flask equipped with a dry ice reflux condenser and a nitrogen inlet were added (at −40° C.) 15 mL of anhydrous hexane, alkene (3–4 mmol) and $SF_5Cl$ (1.2 equiv). The solution was stirred at this temperature for 5 minutes and then $Et_3B$ (0.1 equiv, 1M in hexane) was added slowly using a syringe. The solution was vigorously stirred for 1 hour at −30° C. to −20° C., and then the mixture was allowed to warm to room temperature.

The mixture was hydrolyzed with aqueous $NaHCO_3$ (10%) and the organic layer dried over $MgSO_4$. The solvent was removed and the crude product was passed through a short column of silica gel, eluting with $CH_2Cl_2$. Removal of solvent in most cases provided the products in essentially pure form without the need for additional purification. The reaction can be worked up by simple evaporation of the hexane to give, in most cases, essentially pure product. No significant impurities are observed by $^1H$, $^{19}F$, or $^{13}C$ NMR; however, optional passage through a short column may be used to eliminate, or reduce, possible traces amounts of $Et_3B$.

Table 1 gives the yields for addition of $SF_5Cl$ to a variety of alkenes. Table 2 gives the results for addition to three typical alkynes. Products containing the $SF_5$ substituent are readily confirmed by the presence of the characteristic $AB_4$ pair of pentuplet and doublet signals in their $^{19}F$ NMR spectra, which along with their $^1H$ and $^{13}C$ spectra allowed unambiguous characterization of all of the products.

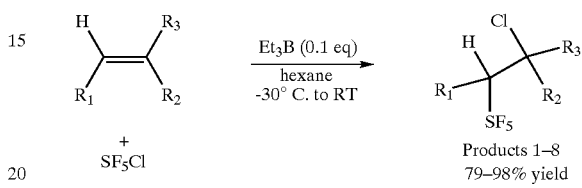

TABLE 1

Yields for addition of $SF_5Cl$ to alkenes[a]

| $R_1$ | $R_2$ | $R_3$ | Product, (% yield) |
|---|---|---|---|
| H | n-$C_6H_{13}$ | H | 1, 95 |
| H | n-$C_4H_9$ | H | 2, 98[19] |
| H | t-$C_4H_9$ | H | 3, 96 |
| H | $C_2H_5$ | $C_2H_5$ | 4, 89 |
| n-$C_3H_7$ | H | n-$C_3H_7$ | 5, 95[b] |
|  | $(CH_2)_4$ | H | 6, 98[b,11] |
| H | p-tolyl | H | 7, 79 |
| H | OAc | H | 8, 98[20] |

[a]in hexane, at −30° C., 0.1 equiv. $Et_3B$, 30 minutes
[b]one major diastereomer (>90% by NMR)

Other examples include, but are not limited to:

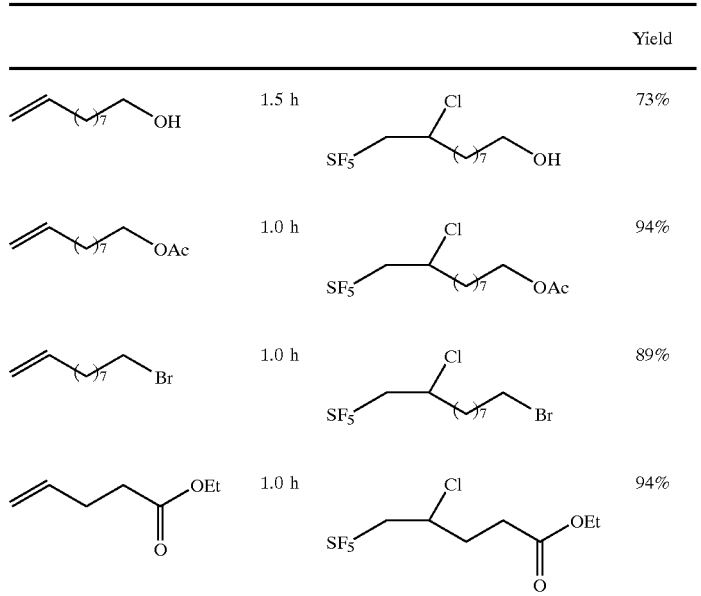

-continued

| | | Yield |
|---|---|---|
| 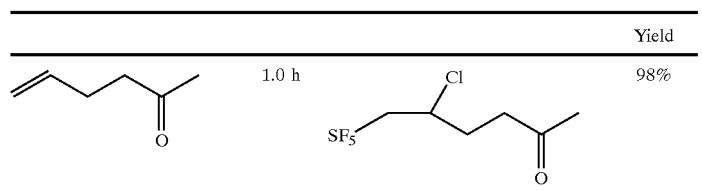 | 1.0 h | 98% |

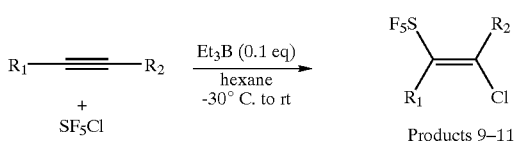

Products 9–11

TABLE 2

Addition of SF$_5$Cl to Alkynes[a]

| R$_1$ | R$_2$ | Product,[b] % yield |
|---|---|---|
| n-C$_3$H$_7$ | n-C$_3$H$_7$ | 9, 93 |
| H | n-C$_6$H$_{13}$ | 10, 94 |
| H | Ph | 11, 94 + 12, 27 |

[a]in hexane, at −30° C., 0.1 equiv. Et$_3$B, 30 minutes
[b]Single diastereomer in each case.

In the reaction with phenyl acetylene, a 2:1 adduct was also obtained in 27% yield. In this case, addition of the propagating radical intermediate to a

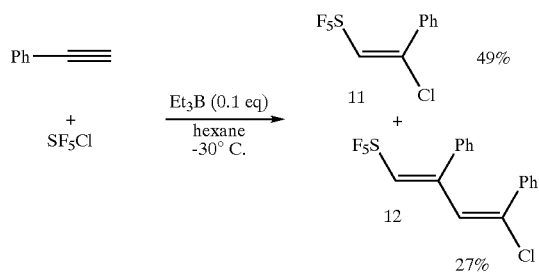

second phenyl acetylene is obviously competing with the chain transfer step. Using a larger excess of SF$_5$Cl in the reaction can minimize this 2:1 product.

The addition reactions are regiospecific and highly diastereoselective, with essentially one product being formed from the additions to cyclohexene, trans-4-octene and the alkynes. Many of the alkyne adducts are novel, although the SF$_5$Cl adduct of propyne has been reported. (Case et al., *J. Chem. Soc.* (1961) 2066–2070.) Although many of the alkene adducts have been reported previously (Case et al., *J. Chem. Soc.* (1961) 2066–2070; Winter et al., *J. Fluorine Chem.* (2001) 107:23–30), styrenes, 2,2-disubstituted alkenes, and non-terminal alkenes had not previously proved to be good substrates for SF$_5$Cl addition.

EXAMPLE 2

SF$_5$ Substituted Aromatic/Alicyclic Compounds

SF$_5$Cl was added to 1,3 cyclohexadiene under the conditions described in Example 1. The resulting adduct was treated with KmnO$_4$/Al$_2$O$_3$ powder (1:1 (w/w)) for two hours at 0° C. SF$_5$ benzene was then recovered in yields of about 60%. In alternative embodiments, substituted cyclohexadienes, or substituted cyclohexenes, can act as substrates in the SF$_5$CL addition reaction. These adducts can, then, be subjected to eliminative or oxidative chemistry to form SF$_5$ aromatics.

EXAMPLE 3

Novel Two-Step Synthesis of Pentafluorosulfanylbenzene

Synthesis of 1-pentafluorosulfanyl-2,4,5-trichlorocyclohexane: A three-necked round bottom flask equipped with a dry ice reflux condenser and a nitrogen inlet was charged with 4,5-dichloro-1-cyclohexane(2.1 g, 0.014M) and 25 mL of dry CH$_2$Cl$_2$. The mixture was cooled to −60° C. and SF$_5$Cl (8.4 g, 0.042M, 3.7 eq.) was added. One and one-half (1.5) mL of a Et$_3$B solution (1M solution in hexane, 0.1 eq.) was slowly added to the mixture using a syringe. Temperature was slowly increased to −30° C. and the mixture was stirred at −30° to −20° C. for four hours. The solvent was evaporated, furnishing an essentially pure product (4.14 g, 0.013M) in a yield of about 94%. The product had the following characteristics: $^1$NMR spectrum (CDCl$_3$, 300 MHz): 4.7 (broad singlet, 1H, CH-SF$_5$), 4.4–4.15 (m, 3H, CHCl), 3–2.4 (m, 4H, CH$_2$); and $^{19}$F NMR spectrum (CDCl$_3$): 82.9 (m, 1F), 57.9 (broad d, 4F).

2. Synthesis of pentafluorosulfanylbenzene: A 100-mL round bottom flask equipped with a water condenser was charged with 1-pentafluorosulfanyl-2,4,5-trichlorocyclohexane (4.1 g, 0.012M) and 60 mL of NaOEt (1.59M solution). The mixture was vigorously stirred at ambient temperature overnight. Water was added, and the solution was extracted with CH$_2$Cl$_2$. The extract was washed with water (3 times) and dried over MgSO$_4$. Evaporation of the solvent furnished a mixture of a liquid and a white solid. The solid was filtered off, leaving pentafluorosulfanylbenzene (1.95 g, ca. 0.01M) in a yield of about 79%. Overall yield calculated from 4,5-dichloro-1-cyclohexene: about 71%. The product had the following characteristics: $^1$H NMR spectrum (CDCl$_3$, 300 MHz): 7.7 (m, 2H) and 7.5 (m, 3H); and $^{19}$F NMR spectrum (CDCl$_3$): 84.6 (q, 1F), 62.8 and 62.4 (4F).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and

We claim:

1. A method of making pentafluorosulfanyl substituted aliphalic or aromatic compounds comprising contacting a solution comprising a solvent, SF5Cl in hexane, and one or more aliphatic or aromatic alkene, alkyne, cyclohexene, or cyclohexadiene compounds with an initiator selected from the group consisting of alkylboranes, irialkylboranes, 9-borabicyclo [3,3.1] nonane, and mixture thereof to produce a reaction product comprising pentafluorosulfanyl substituted compound.

2. The method according to claim 1, wherein said aliphatic or aromatic alkene, alkyne, cyclohexene, or cyclohexadiene compounds are substituted.

3. The method according to claim 1, wherein said compound is cyclohexene, substituted cyclohexene, cyclohexadiene, or substituted cyclohexadiene and wherein said reaction product is a pentafluorosulfanyl substituted adduct.

4. The method according to claim 3, further comprising the step of eliminating or oxidizing said pentafluorosulfanyl substituted adduct to form a pentafluorosulfanyl substituted aromatic compound.

5. The method according claim 1, further comprising the step of hydrolyzing said pentafluorosulfanyl substituted compound.

6. The method according to claim 5, further comprising the step of drying said hydrolyzed pentafluorosulfanyl substituted compound.

7. The method according to claim 6, wherein said drying step is performed over a desiccant.

8. The method according to claim 1, further comprising the step of purifying said pentafluorosulfanyl substituted compound.

9. The method according to claim 4, further comprising the step of purifying said pentafluorosulfanyl substituted aromatic compound.

10. The method according to claim 5, further comprising the step of purifying said hydrolyzed pentafluorosulfanyl substituted compound.

11. The method according to claim 6, further comprising the step of purifying said dried and hydrolyzed pentafluorosulfanyl substituted compound.

12. The method according to claim 1, wherein said solution comprises: solvent, $SF_5Cl$, and initiator and wherein said solution is contacted with one or more compounds; or said solution comprises: solvent and $SF_5Cl$ and wherein said solution is contacted with one or more compounds and said initiator.

* * * * *

UNITED STATES PATENT AND TRADEMARK OFFICE
CERTIFICATE OF CORRECTION

PATENT NO.    : 6,919,484 B2
DATED         : July 19, 2005
INVENTOR(S)   : William R. Dolbier, Jr. et al.

It is certified that error appears in the above-identified patent and that said Letters Patent is hereby corrected as shown below:

Column 4,
Line 49, "injection of said compounds" should read -- reaction of said compounds --.
Line 54, "Opiionally, the" should read -- Optionally, the --.
Line 55, "climination" should read -- elimination --.

Column 8,
Line 28, "4,5-dichloro-1-cyclohexane(2.1 g, 0.014M)" should read
-- 4,5-dichloro-1-cyclohexane (2.1 g, 0.014M) --.
Line 38, "$^1$NMR spectrum" should read -- $^1$N MR spectrum --.

Column 9,
Lines 11-12, "irialkylboranes, 9-borabicyclo [3, 3.1]" should read -- dialkylboranes, trialkylboranes, 9-borabicyclo[3.3.1] --.

Signed and Sealed this

Thirteenth Day of December, 2005

JON W. DUDAS
*Director of the United States Patent and Trademark Office*

UNITED STATES PATENT AND TRADEMARK OFFICE
CERTIFICATE OF CORRECTION

PATENT NO.    : 6,919,484 B2
DATED         : July 19, 2005
INVENTOR(S)   : William R. Dolbier, Jr. et al.

It is certified that error appears in the above-identified patent and that said Letters Patent is hereby corrected as shown below:

<u>Column 8,</u>
Line 28, "4,5-dichloro-1-cyclohexane(2.1 g, 0.014M)" should read
-- 4,5-dichloro-1-cyclohexene (2.1 g, 0.014M) --.

Signed and Sealed this

Seventh Day of March, 2006

JON W. DUDAS
*Director of the United States Patent and Trademark Office*